(12) United States Patent
Inami

(10) Patent No.: US 6,417,658 B1
(45) Date of Patent: Jul. 9, 2002

(54) FLOW CELL FOR PARTICLE ANALYZER USING ELECTRICAL SENSING ZONE METHOD

(75) Inventor: Keiichi Inami, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/616,889

(22) Filed: Jul. 14, 2000

(30) Foreign Application Priority Data

Jul. 16, 1999 (JP) .......................................... 11-203282

(51) Int. Cl.⁷ .............................................. G01N 27/00
(52) U.S. Cl. ...................... 324/71.4; 324/71.1; 324/438; 73/865.5
(58) Field of Search ............................... 324/71.1, 71.4, 324/438, 439, 466, 449, 699, 453; 73/865.5; 377/449, 12, 11

(56) References Cited

U.S. PATENT DOCUMENTS

| | | | | |
|---|---|---|---|---|
| 4,484,134 A | * | 11/1984 | Halloran | .................... 324/71.1 |
| 4,564,803 A | * | 1/1986 | Loren | ......................... 324/71.1 |
| 4,901,024 A | * | 2/1990 | Miyake | ....................... 324/438 |
| RE36,074 E | * | 2/1999 | Kouzuki | ..................... 324/71.4 |

FOREIGN PATENT DOCUMENTS

| | | |
|---|---|---|
| JP | A815125 | 1/1996 |

* cited by examiner

*Primary Examiner*—Michael J. Sherry
*Assistant Examiner*—Trung Nguyen

(57) ABSTRACT

A flow cell for a particle analyzer using an electrical sensing zone method, includes: a detecting member having a through hole; a first cell for supplying a particle containing liquid to the through hole; a second cell for receiving and discharging the particle containing liquid that has passed through the through hole; electrodes provided in the first cell and the second cell respectively, for supplying an electrical current to the liquid passing through the through hole; and a sliding member for sliding at least one of the first and second cells to change a distance therebetween; wherein the first and second cells cooperate with the sliding member to detachably sandwich the detecting member therebetween so that the detecting member is connected to the first and second cells in a watertight state.

8 Claims, 7 Drawing Sheets

FLOW CELL FOR PARTICLE ANALYZER USING ELECTRICAL SENSING ZONE METHOD

CROSS-REFERENCE TO RELATED APPLICATION

This application is related to Japanese application No. 11-203282 filed on Jul. 16, 1999, whose priority is claimed under 35 USC §119, the disclosure of which is incorporated by reference in its entirety.

BACKGROUND OF THE INVENTION

1. Field of the Invention

The present invention relates to a flow cell for a particle analyzer using an electrical sensing zone method. More particularly, it relates to a flow cell for a particle analyzer that employs, for the measurement in size and number of powdery particles such as fine ceramic particles, pigments and cosmetic powders, an electrical sensing zone method in which a particle containing liquid is passed through an aperture so that particles in the liquid are measured based on changes in electrical impedance, and a so-called sheath flow method in which a flow of the particle containing liquid is enclosed by a sheath liquid to pass through the aperture.

2. Description of Related Art

The electrical sensing zone method has been utilized to measure in size and number of blood cells in blood or industrial particles such as cement powders, latexes and toners. In this method, a barrier having an aperture is provided in an electrolyte solution, electrodes are arranged to sandwich the aperture, and subject particles dispersed in the solution are passed through the aperture. When the particle passes through the aperture, an electrical resistance between the electrodes is instantaneously changed and a voltage pulse is generated. The height of the voltage pulse reflects the particle volume, so that a spherical equivalent diameter can be measured regardless of its shape. From the measurement, the volume-based particle size of the sample particles can be obtained. Further, the number of the particles can be counted from the number of the pulses.

In the electrical sensing zone method, the height of the voltage pulse varies depending on a position in the aperture where the particle passes through. Further, a plurality of particles passing together through the aperture may be measured as one particle, or the particles that have passed through the aperture may stay near the aperture and cause noise. To solve these demerits, the sheath flow method has customarily been employed. In a particle size distribution measurement utilizing the sheath flow method, a flow of the particle containing liquid in the flow cell is enclosed with another liquid (sheath liquid) flow to narrow down the particle containing liquid flow so as to introduce the particles in a row into the approximate center of the aperture. Accordingly, the particle size can be obtained with less margin of error.

There is a limitation to the measurable size of the particle in the electrical sensing zone method depending on the diameter of the aperture. For example, where the size of the particle is less than 1/50 of the aperture diameter, the signal from the particle is hard to be distinguished from the noise. On the contrary, where the size of the particle is too great, the pulse height and the particle volume lose their linearity, and the aperture tends to be clogged. To replace the flow cell to change the aperture diameter requires removal and attachment of wirings led to the electrodes and pipes connected to the flow cell. Further, where the subject particles have a wide particle size distribution, the measurement will be complicated.

As means to deal with the above demerits, there has been known a measuring apparatus comprising a flow cell which can be divided into two segments and a detecting member sandwiched therebetween, the detecting member having an aperture through which a sheath liquid enclosing a particle containing liquid can pass (for example, see Japanese Unexamined Patent Publication No. HEI 8-15125). The detecting member includes a detachable member sealingly connected to the segments. As the detachable member, both sides of the detecting member are formed each with a thread of the opposite hand so that the detecting member can be removed from the segments by rotating the detecting member only, without rotating the segments.

However, in such a conventional particle measuring apparatus, in the step of attaching the detecting member to the separated segments again, it is difficult to thread both sides of the detector into the segments to the same extent. If one side is tightly threaded before the other side is not threaded enough, the other side loses the watertightness.

SUMMARY OF THE INVENTION

The present invention has been achieved in view of the above circumstances, and provides a particle measuring apparatus capable of easy and ensured replacement of the detecting member in the flow cell.

The present invention provides a flow cell for a particle analyzer using an electrical sensing zone method, comprising: a detecting member having a through hole; a first cell for supplying a particle containing liquid to the through hole; a second cell for receiving and discharging the particle containing liquid that has passed through the through hole; electrodes provided in the first cell and the second cell respectively, for supplying an electrical current to the liquid passing through the through hole; and a sliding member for sliding at least one of the first and second cells to change a distance therebetween; wherein the first and second cells cooperate with the sliding member to detachably sandwich the detecting member therebetween so that the detecting member is connected to the first and second cells in a watertight state.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

In the flow cell of the present invention, the sliding member is provided to slide at least one of the first cell and the second cell to bring them closer to each other or separate them from each other. When the first and second cells are brought closer, the detecting member is sandwiched therebetween to be connected to them, and when the first and second cells are separated from each other, the detecting member is isolated from them. Thus, the replacement of the detecting member can be easily performed.

That is, when the detecting member is spaced from the first and second cells by the sliding member, the detecting member having the through hole is replaceable with another detecting member having a through hole of a different diameter.

The present invention may further comprise a fixing member for fixing the cell on the sliding member, by which the detecting member can more surely be sandwiched between the first and second cells.

The detecting member may comprise an engaging member for detachably engaging with the sliding member, by which the detecting member can easily be aligned relative to the first and second cells upon the replacement thereof.

The detecting member is preferably adapted to be arranged between the first and second cells in a specific position, by which the detecting member is prevented from being arranged upside down.

The sliding member may comprises a plurality of parallel shafts (e.g., two shafts) projecting from one of the first and second cells and the other cell has a plurality of openings (two holes in this case) for receiving the parallel shafts, and thereby the sliding member can easily and firmly be constructed.

In this case, the detecting member may have U-shaped grooves for detachably fitting with the parallel shafts to slide along them.

The U-shaped grooves may be different in groove width. The parallel shafts preferably have sectional sizes that can fit into the corresponding U-shaped grooves, by which the detecting member is prevented from being arranged upside down.

EXAMPLE

Hereinafter, the present invention will be detailed by way of example with reference to the drawings, but the invention is not limited thereto.

Figure 1:
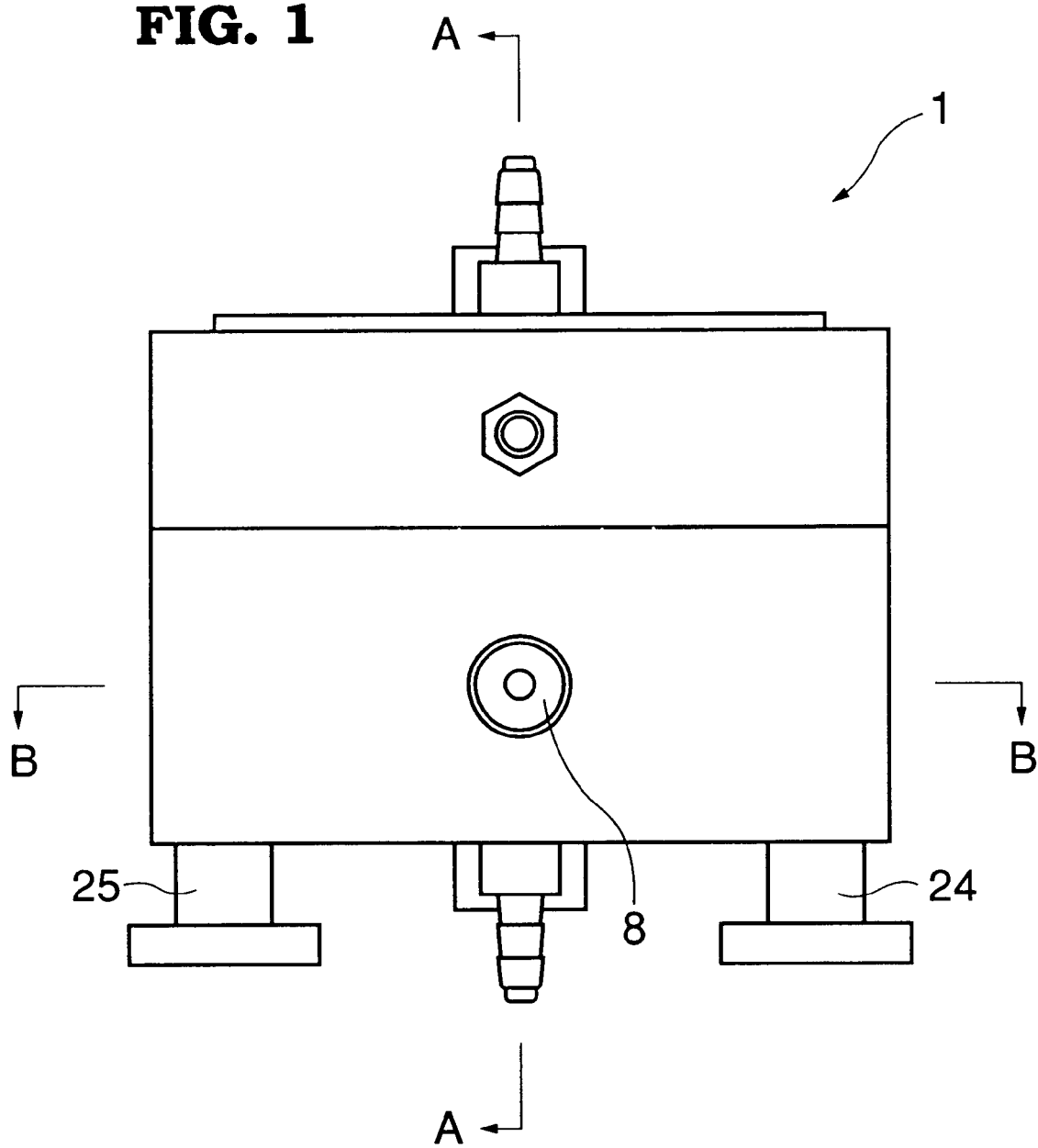
FIG. 1 is a top plan view illustrating a flow cell according to the present invention.
Figure 2:
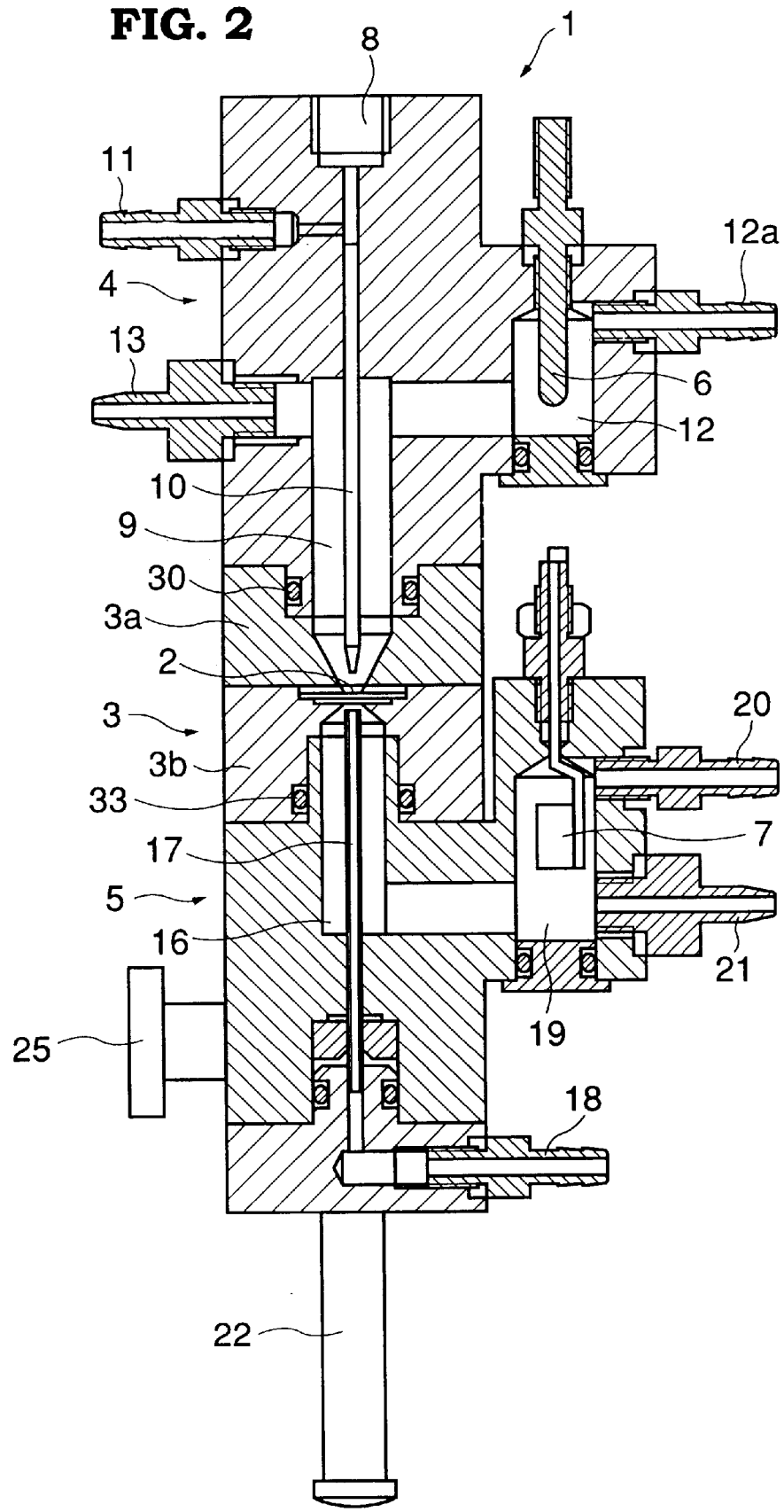
FIG. 2 is a cross sectional view taken along the arrow A—A of FIG. 1.
Figure 3:
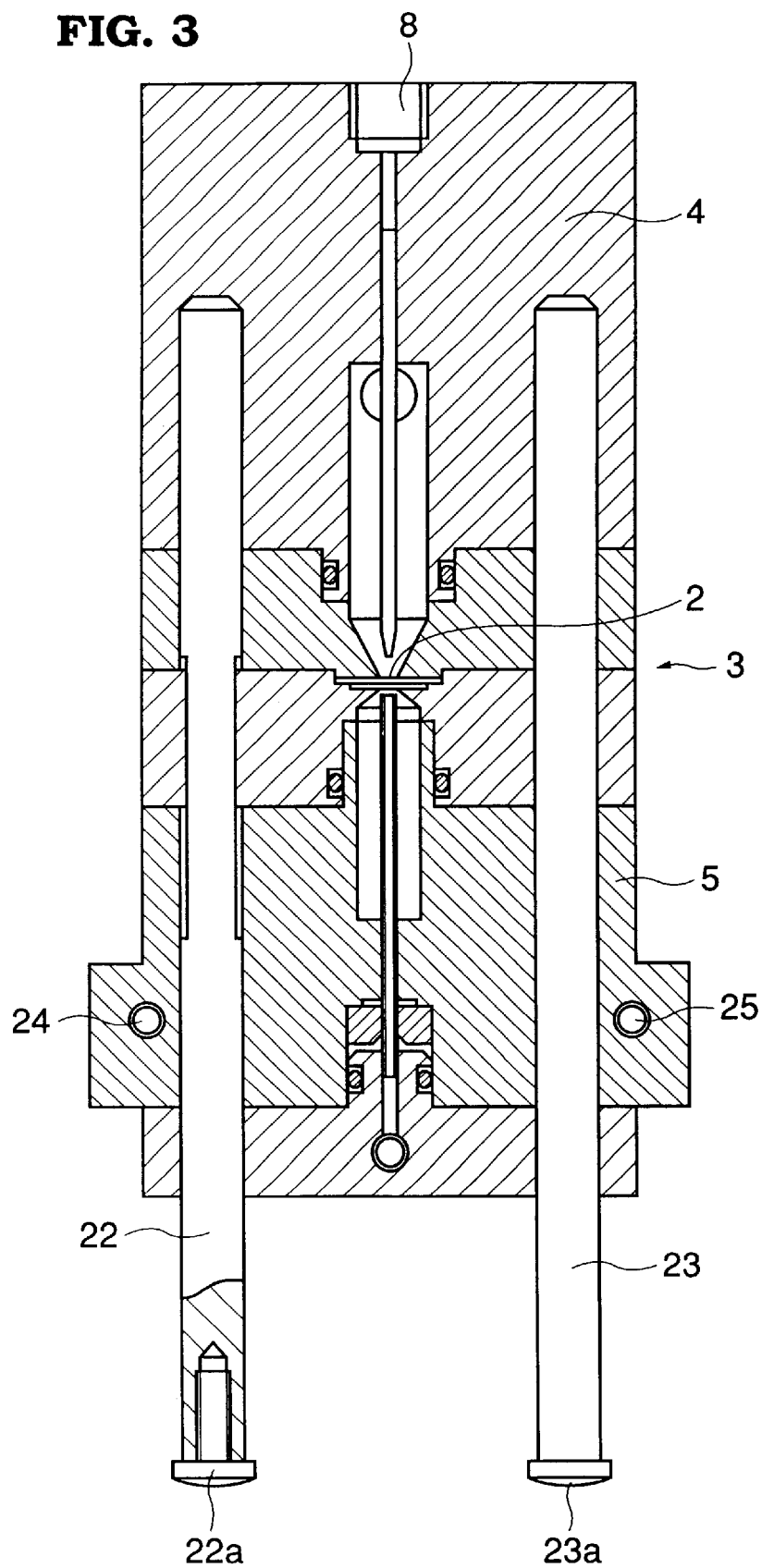
FIG. 3 is a cross sectional view taken along the arrow B—B of FIG. 1.
Figure 4:
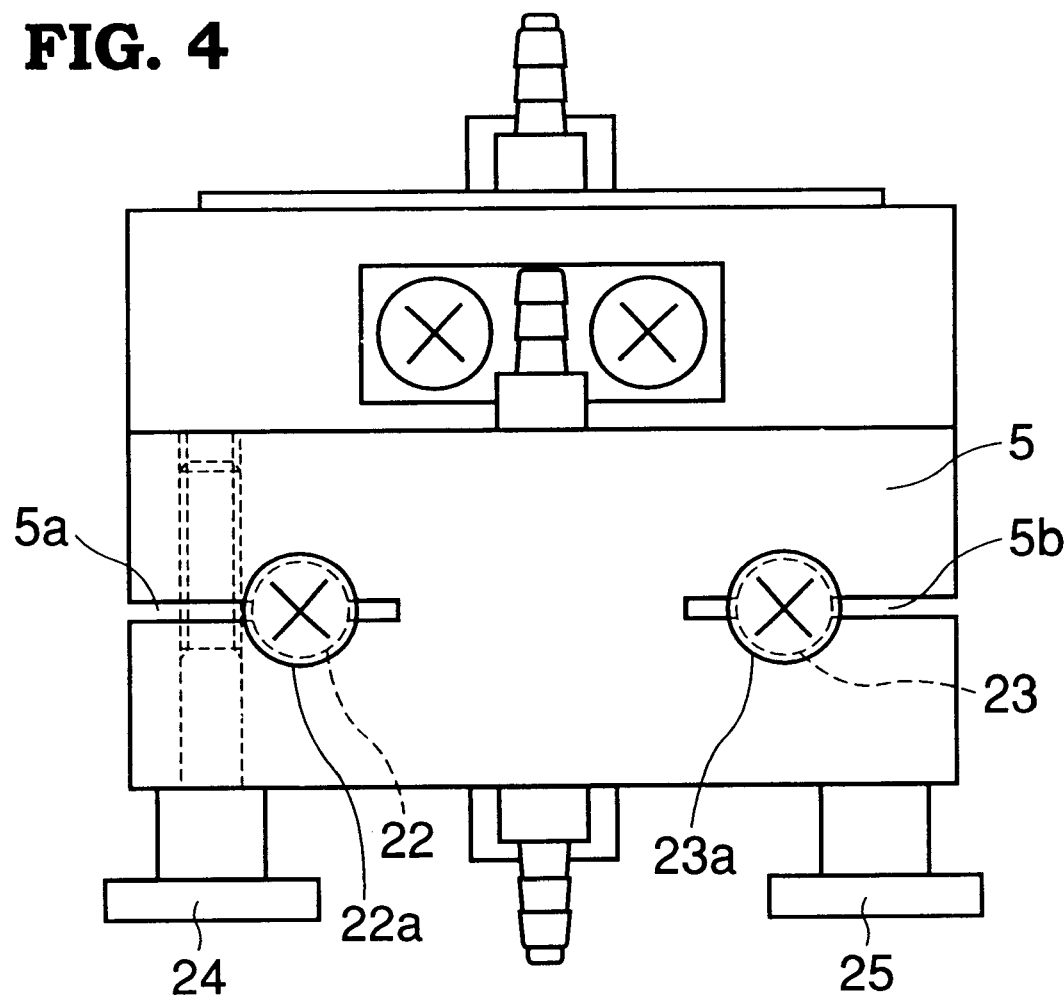
FIG. 4 is a bottom plan view of the flow cell shown in FIG. 1.

FIG. 1 shows a top plan view of a sheath flow cell as the particle measuring apparatus of the present invention, FIG. 2 is a sectional view taken along the arrow A—A of FIG. 1, FIG. 3 is a sectional view taken along the arrow B—B of FIG. 1 and FIG. 4 is a bottom plan view of the sheath flow cell.

As shown in FIG. 2, a flow cell 1 comprises a detecting member 3 having an aperture (through hole) 2 for detecting particles, a first cell 4 for supplying a particle containing liquid enclosed with a sheath liquid to the aperture 2, a second cell 5 for discharging the particle containing liquid and the sheath liquid that have passed through the aperture 2 and electrodes 6 and 7 provided in the first cell 4 and the second cell 5, respectively. Electrodes 6 and 7 are connected to a constant current d.c. power source (not shown) and supply an electrical current to the liquid passing through the aperture 2.

The first cell 4 forms on the top thereof a connection hole 8 to be connected with a tube for injecting a particle containing liquid (hereinafter referred to as a sample) and on the sides thereof nipples 11, 12a and 13 to be connected with an outer fluid circuit (described later). Cavity portions 9 and 12 are provided inside the cell 4, and the connection hole 8 and the nipple 11 are connected to a proximal end of a jet nozzle 10 coaxially projecting downward in the cavity portion 9. A distal end of the jet nozzle 10 reaches the proximity of the aperture 2. The cavity portions 9 and 12 are communicated with each other. The electrode 6 is provided in the cavity portion 12 which is connected to the nipple 12a.

Figure 8:
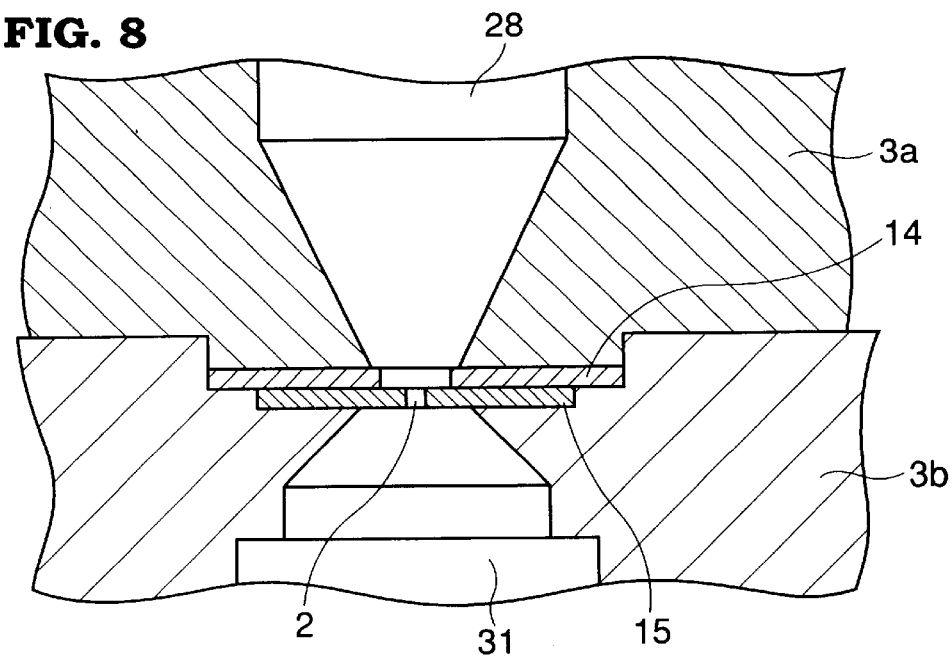
FIG. 8 is an enlargement of a major part of FIG. 5.

The detecting member 3 comprises an upper block 3a and a lower block 3b that are integrally fixed to each other with screws (not shown). The aperture 2 is opened in the center of a disc 15 pressed by a packing 14 between the upper block 3a and the lower block 3b as seen in FIG. 8.

The second cell 15 is provided with cavity portions 16 and 19 in the inside thereof and nipples 18, 20 and 21 on the outside thereof. A collection pipe 17 projecting upwardly is provided in the cavity portion 16, a proximal end thereof is conneted to the nipple 18 and a distal end thereof reaches the proximity of the aperture 2. The cavity portions 16 and 19 are connected to each other. The electrode 7 is provided in the cavity portion 19 which is connected to the nipples 20 and 21.

As shown in FIG. 3, the second cell 5 is slidably supported by two parallel shafts 22 and 23 of the same diameter projecting downward from the first cell 4 as a sliding member. The detecting member 3 is sandwiched between the first cell 4 and the second cell 5.

As shown in FIG. 4, the second cell 5 includes elongate slits 5a and 5b and bolts 24 and 25 each having a handle that are screwed orthogonally to the slits 5a and 5b. Tightening the bolts 24 and 25 reduces the widths of the slits 5a and 5b, so that the second cell 5 can be fixed to the shafts 22 and 23.

On the other hand, loosening the bolts 24 and 25 makes the second cell 5 slidable along the shafts 22 and 23, so that the second cell 5 can be moved to abut stopper screws 22a and 23a provided at the distal ends of the shafts 22 and 23.

Figure 5:
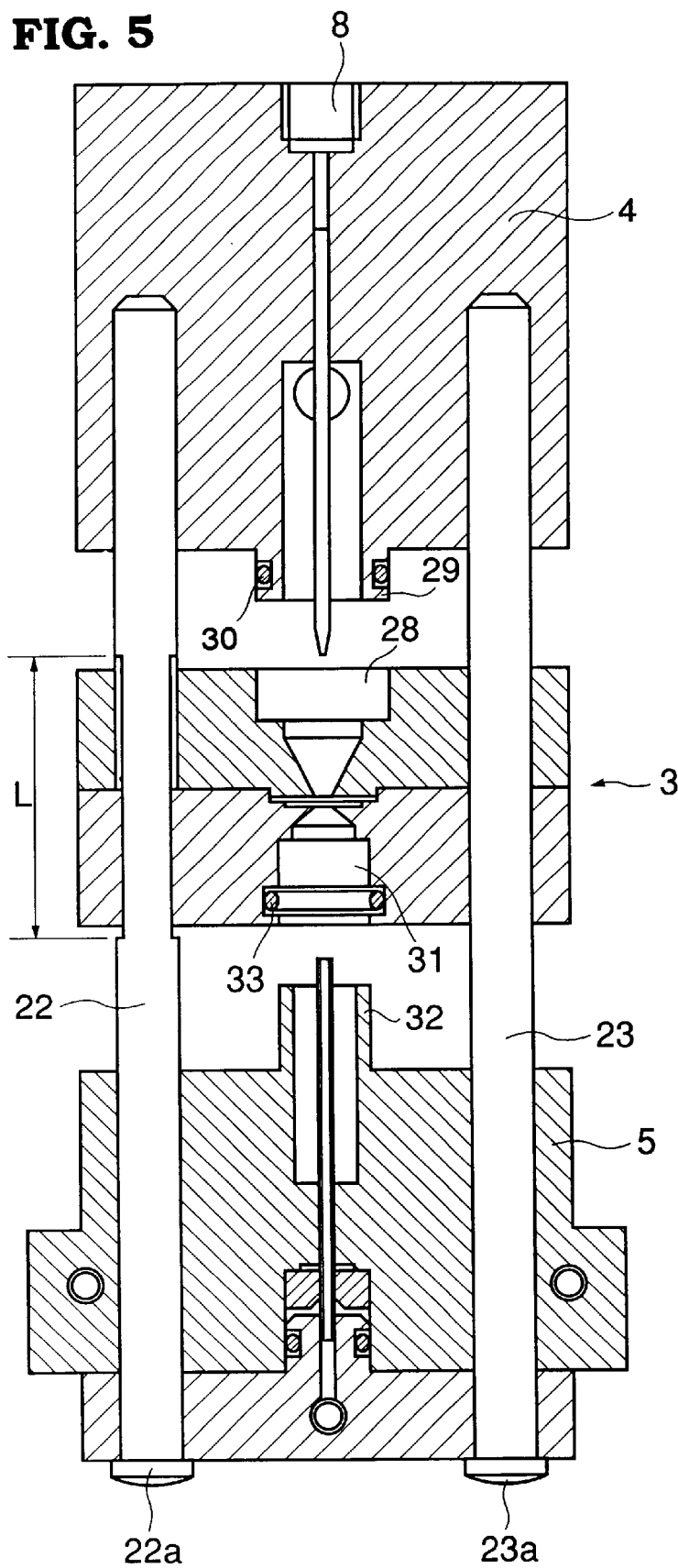
FIG. 5 is a view corresponding with FIG. 3, indicating when to replace a detecting member in the flow cell according to the present invention.
Figure 6:
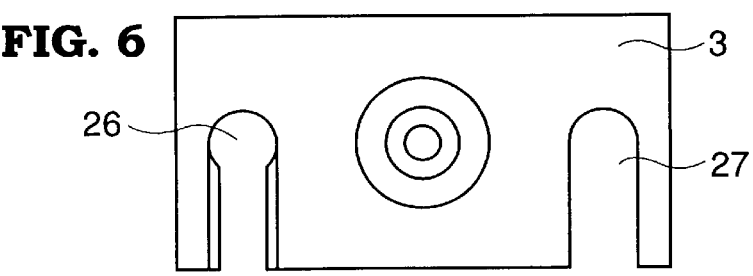
FIG. 6 is a top plan view illustrating the detecting member according to the present invention.
Figure 7:
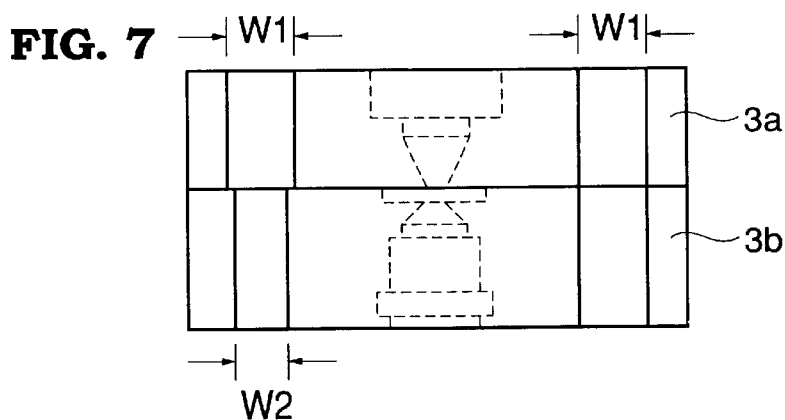
FIG. 7 is a front view of the detecting member according to the present invention.

By sliding the second cell 5 and the detecting member 3 to the positions as shown in FIG. 5, the detecting member 3 can be removed from the shafts 22 and 23 in a vertical direction to the drawing sheet for the replacement thereof. That is, as shown in FIGS. 6 and 7, the detecting member 3 has U-shaped grooves 26 and 27 for fitting with the shafts 22 and 23, respectively. The width of the groove 27 is W1 in both the upper block 3a and the lower block 3b to fit with the shaft 23. The width of the groove 26 in the upper block 3a is W1 to fit with the shaft 22, but in the lower block 3b the width is W2 which is smaller than W1.

Corresponding to the above, as shown in FIG. 5, the shaft 22 in a region L is thinned to have opposite plane sides so as to fit into the U-shaped groove having the width of W2.

The structural relationship between the U-shaped grooves 26 and 27 and the shafts 22 and 23 is established to prevent the detecting member 3 from being arranged upside down at the replacement thereof.

After the replacement of the detecting member 3 in the state shown in FIG. 5, the detecting member 3 is slid along the shafts 22 and 23 toward the first cell 4 to fit a convex portion 29 of the first cell 4 into a concave portion 28 of the detecting member 3. Thus, the first cell 4 and the detecting member 3 are connected and an O-ring 30 gives the watertightness to the connection. Next, the second cell 5 is slid along the shafts 22 and 23 toward the detecting member 3 to fit a convex portion 32 of the second cell 5 into a concave portion 31 of the detecting member 3. Thus, the second cell 5 and the detecting member 3 are connected and an O-ring 33 gives the watertightness to the connection. Then, if the bolts 24 and 25 are tightened to fix the second cell 5 on the shafts 22 and 23, the apparatus turns back into a state shown in FIG. 3.

In this example, the detecting member 3, the first cell 4 and the second cell 5 (FIG. 2) are made of a material which is easy to cut and highly chemical-resistant such as PET (polyethylene terephthalate). The jet nozzle 10 and the collection pipe 17 (FIG. 2) are constituted of ceramic pipes. The disc 15 having he aperture 2 (FIG. 8) is an artificial ruby disc having a thickness of 0.4 mm and a diameter of 6 mm. A plurality of kinds of detecting members 3 are provided, in which the apertures 2 are sequentially doubled in area within a diameter range of 30 to 300 $\mu$m. The electrodes 6 and 7 are made of stainless steel and platinum, respectively.

Figure 9:
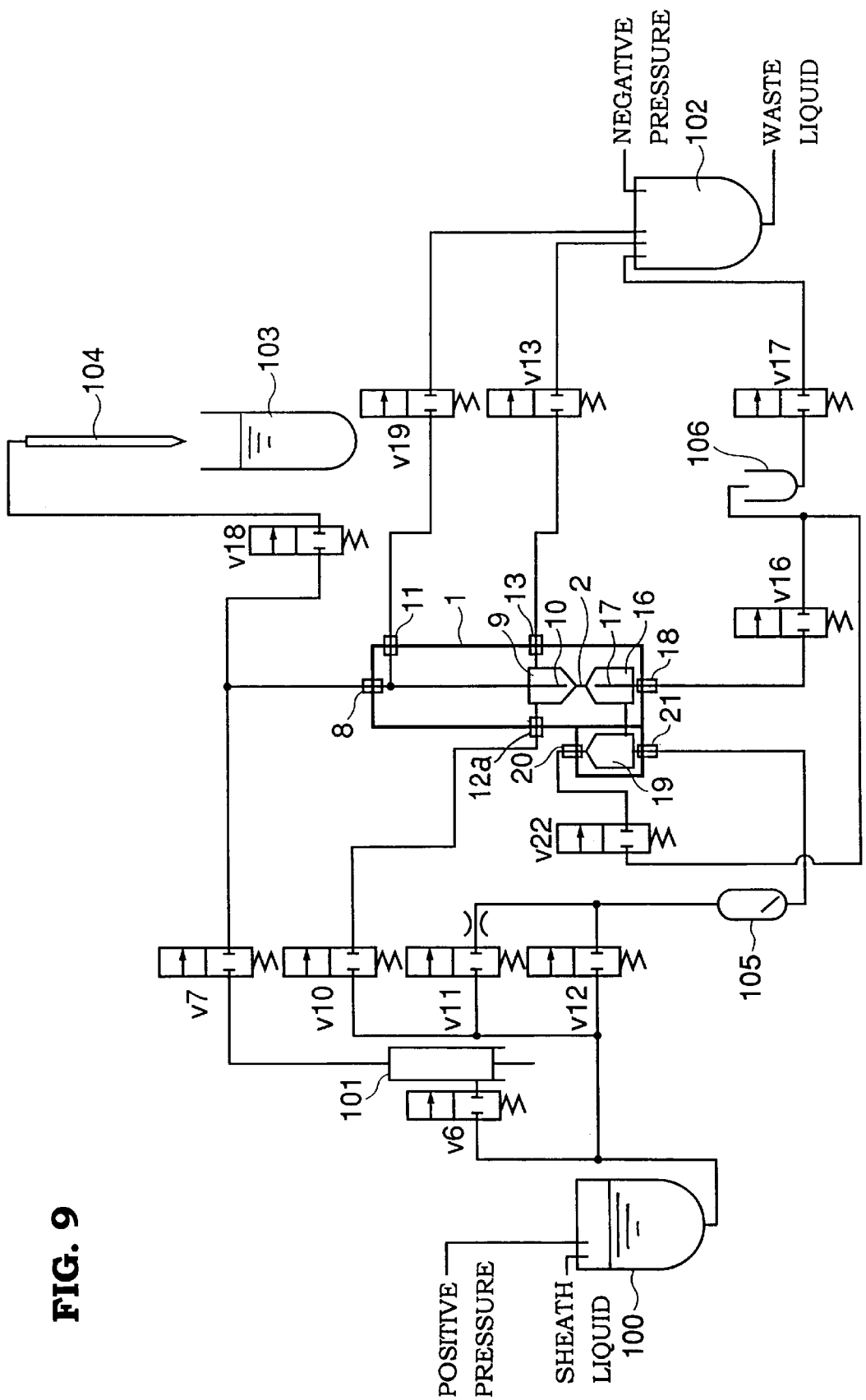
FIG. 9 is a fluid circuit for the particle measurement using the flow cell according to the present invention.

Referring to FIGS. 2 and 9, a fluid circuit to perform a particle measurement using the flow cell 1 is explained hereinafter.

Referring to FIG. 9, first, valves V6, V7 and V19 are turned ON to supply a sheath liquid to a syringe route starting from a sheath liquid chamber 100 through the valve V6, a syringe 101, the valve V7 and the valve 19 to a waste chamber 102 in order to remove bubbles from the route. A positive pressure is applied to the sheath liquid chamber 100 and a negative pressure is applied to the waste chamber 102.

Next, valves V10 and V13 are turned ON to supply the sheath liquid to a front sheath liquid route in order to remove bubbles from the route. After a certain period, these valves are all closed.

Then, valves V12, V16, V17 and V22 are turned ON to supply the sheath liquid to a back sheath liquid route in order to remove bubbles from the route. After a certain period, these valves are all closed. An insulating chamber 105 is provided between the valves 11, 12 and the flow cell 1, and an insulating chamber 106 is provided between the valve V16 and the valve V17.

Then, valves V18 and V19 are turned ON to introduce the sample from a sample chamber 103 into a route between the valves V18 and V19 using a pipette 104. After the introduction, the valves V18 and V19 are turned OFF.

Then, the valves V10, V11 and V16 are turned ON to supply a front sheath liquid into the cavity portion 9 and a back sheath liquid to the cavity portion 16 (FIG. 2). Simultaneously, the valve V7 is turned ON and the syringe 101 is operated so that the sample contained in the route between the valves V18 and V19 is discharged from the jet nozzle 10 (FIG. 2) by the pressure generated by the operation of the syringe 101. The discharged sample is enclosed with the front sheath liquid and passes through the aperture 2. The passed sample and the front sheath liquid are further enclosed with the back sheath liquid and discharged though the collection pipe 17 and the valve V16 into the insulating chamber 106. The waste liquid held in the insulating chamber 106 is discharged into the waste chamber 102 by turning the valve V17 ON.

When the sample enclosed with the front sheath liquid is passed through the aperture 2, a change in impedance between the electrodes 6 and 7 (FIG. 2) is measured by a measurement device (not shown). After the measurement is completed, the syringe 101 is stopped working. Simultaneously, the valve V19 is turned ON to pass the sheath liquid backward in the jet nozzle 10 for a certain period to wash the jet nozzle 10.

The front and back sheath liquids are kept passing for a certain period to wash the flow cell 1. After a certain period, the valves V10, V11, V16 and V17 are closed to finish the washing of the flow cell 1. After the washing of the jet nozzle 10 is finished, the valve V19 is turned OFF and the valves V6, V7 and V18 are turned ON to wash the sample introduction route and the pipette 104. The washing is finished after a certain period by turning the valves V6, V7 and V18 OFF.

According to the present invention, the detecting member having the aperture for the particle measurement is sandwiched between the first cell and the second cell that are slidably supported, so that the detecting member can easily be replaced by slidingly separating the first and second cells from the detecting member.

What is claimed is:

1. A flow cell for a particle analyzer using an electrical sensing zone method, comprising:
   a detecting member having a through hole;
   a first cell for supplying a particle containing liquid to the through hole;
   a second cell for receiving and discharging the particle containing liquid that has passed through the through hole;
   electrodes provided in the first cell and the second cell respectively, for supplying an electrical current to the liquid passing through the through hole; and
   a sliding member for sliding at least one of the first and second cells to change a distance therebetween;
   wherein the first and second cells cooperate with the sliding member to detachably sandwich the detecting member therebetween so that the detecting member is connected to the first and second cells in a watertight state.

2. A flow cell according to claim 1, wherein the detecting member is adapted to be arranged between the first and second cells in a specific position.

3. A flow cell according to claim 1 further comprising a fixing member for fixing the at least one of the first and second cells to the sliding member.

4. A flow cell according to claim 1, wherein the detecting member includes an engaging portion for detachably engaging with the sliding member.

5. A flow cell according to claim 1, wherein the sliding member comprises a plurality of parallel shafts projecting from one of the first and second cells and the other cell has a plurality of openings which the shafts pass through.

6. A flow cell according to claim 5, wherein the detecting member includes a plurality of U-shaped grooves for detachably fitting with the plurality of parallel shafts, respectively.

7. A flow cell according to claim 6, wherein the plurality of U-shaped grooves have different widths, and the plurality of parallel shafts each have a sectional size that fits into the corresponding U-shaped groove.

8. A flow cell according to claim 1, wherein when the detecting member is spaced from the first and second cells by the sliding member, the detecting member having the through hole is replaceable with another detecting member having a through hole of a different diameter.

* * * * *